US008628651B2

(12) United States Patent
Dhawan et al.

(10) Patent No.: US 8,628,651 B2
(45) Date of Patent: Jan. 14, 2014

(54) ELECTROPHORETIC DEVICE FOR SEPARATION OF CHARGED MOLECULES USING A PETRI DISH

(75) Inventors: Alok Dhawan, Lucknow (IN); Hari Om Mishra, Lucknow (IN); Alok Kumar Pandey, Lucknow (IN); Mahima Bajpayee, Lucknow (IN); Devendra Parmar, Lucknow (IN); Mukul Das, Lucknow (IN)

(73) Assignee: Council of Scientific & Industrial Research, New Delhi, IN (US)

( * ) Notice: Subject to any disclaimer, the term of this patent is extended or adjusted under 35 U.S.C. 154(b) by 82 days.

(21) Appl. No.: 12/935,471

(22) PCT Filed: Mar. 31, 2009

(86) PCT No.: PCT/IN2009/000216
§ 371 (c)(1),
(2), (4) Date: May 20, 2011

(87) PCT Pub. No.: WO2009/122446
PCT Pub. Date: Oct. 8, 2009

(65) Prior Publication Data
US 2011/0247935 A1    Oct. 13, 2011

(30) Foreign Application Priority Data
Mar. 31, 2008 (IN) .............................. 847/DEL/2008

(51) Int. Cl.
*G01N 27/447* (2006.01)
*G01N 27/453* (2006.01)
(52) U.S. Cl.
USPC ......................................... 204/466; 204/617

(58) Field of Classification Search
USPC ......... 204/400, 456, 457, 458, 600, 605–615, 204/617, 466
See application file for complete search history.

(56) References Cited

U.S. PATENT DOCUMENTS

2005/0082168 A1 * 4/2005 Kang ............................ 204/456
2006/0078984 A1 * 4/2006 Moyle et al. ................ 435/287.2

FOREIGN PATENT DOCUMENTS

EP        1217367 A1 * 6/2002
JP        61003041      * 1/1986
JP        61003041 A  * 1/1986

OTHER PUBLICATIONS

Wang et al., "Controlling nanoparticle distribution in hydrogel by electrophopresis for gradient refractive index lens applications," Organic Photonic Materials and Devices VII, edited by James G. Grote, Toshikuni Kaino, François Kajzar, Proceedings of SPIE vol. 5724 (SPIE, Bellingham, WA, 2005), pp. 344-351.*
Full English language translation of Tokida et al. JP 61003041 A, patent published Jan. 9, 1986.*
Alok Dhawan, et al; "The effect of smoking and eating habits on DNA damage in Indian population as measured in the Comet assay", Mutation Research, vol. 474, pp. 121-128; Acceped Dec. 12, 2000.

(Continued)

*Primary Examiner* — Alex Noguerola
(74) *Attorney, Agent, or Firm* — Ladas & Parry LLP

(57) ABSTRACT

The present invention provides a portable circular electrophoretic device having uniform electric field over a small surface area. It also provides a multidirectional process of electrophoresis for separation of charged molecules thereby increasing the resolution of macromolecules.

12 Claims, 4 Drawing Sheets

(56) References Cited

OTHER PUBLICATIONS

Laura H. Carreira, et al; "Construction and Application of a Modified "Gene Machine": A Circular Concentrating Preparative Gel Electrophoresis Device Employing Discontinuous Elution", Analytical Biochemistry, vol. 106, Issue 2, pp. 455-468, Aug. 1980.

Techware Equipment GeNei™; "Rod Gel Electrophoresis Systems", 1 page; Bangalore Genei Catalogue, Published 2008.
International Search Report mailed Aug. 20, 2009; PCT/IN2009/000216.

* cited by examiner

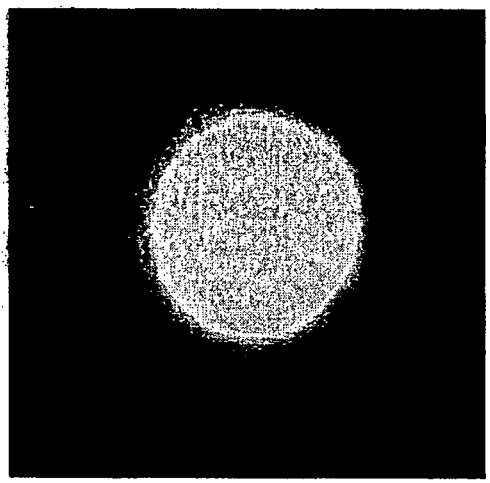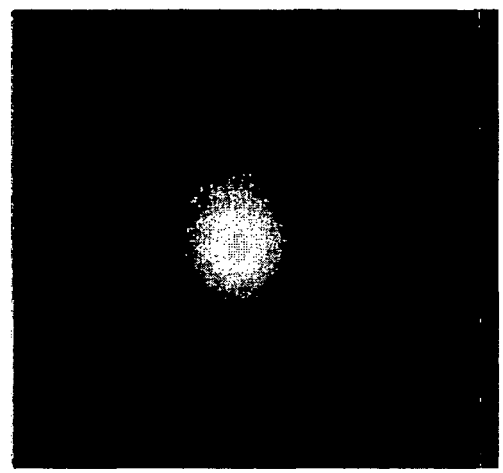
Figure 2

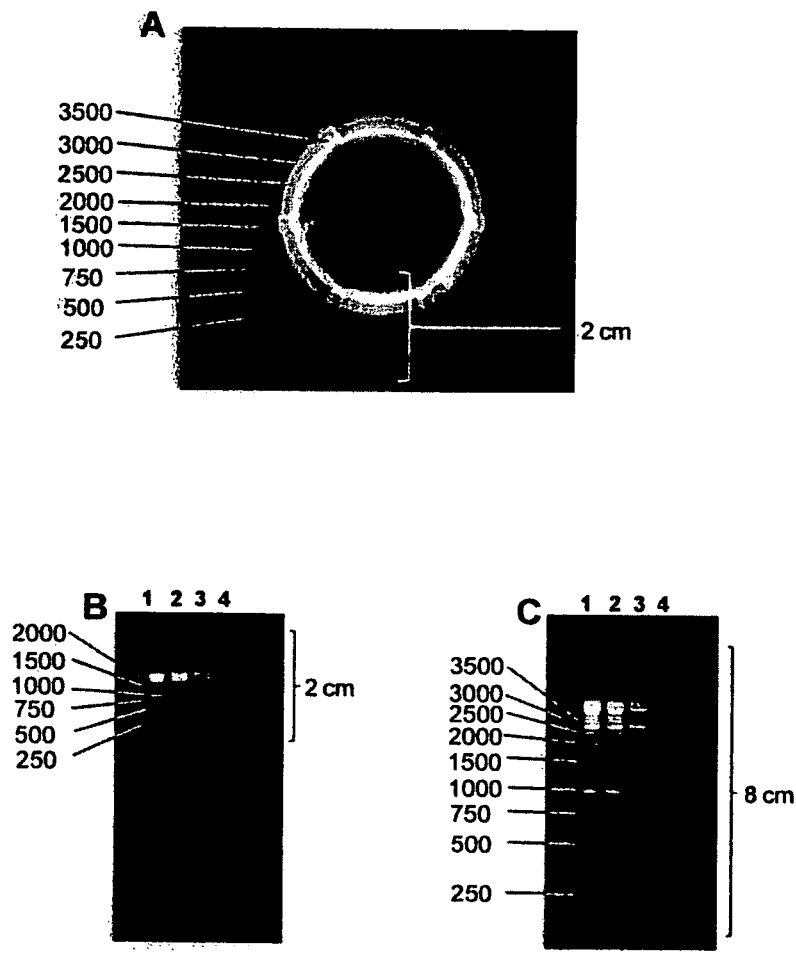

Figure 3: DNA gel electrophoresis in 1% agarose, showing bands of different sizes (base pair) (A) 2μg of DNA loaded into the well and run at 10mA/10V (constant current) for 1 hour in the circular electrophoretic chamber. Distance travelled by DNA was 2cm; (B) Lanes 1, 2, 3, 4 containing 2,1,0.5,0.3 μg of DNA respectively were run for 2cm at 120V/55mA (constant voltage) in the horizontal gel apparatus; (C) lanes 1, 2, 3, 4 containing 2, 1, 0.5, 0.3 μg of DNA respectively were run for 8cm at 120V/55mA (constant voltage) in the horizontal gel apparatus.

Figure 3

ELECTROPHORETIC DEVICE FOR SEPARATION OF CHARGED MOLECULES USING A PETRI DISH

FIELD OF INVENTION

The present invention relates to a circular electrophoretic device for separation of charged molecules. More particularly a portable device to facilitate high resolution of molecules based on charge and weight of molecules in a multidirectional manner and its process thereof is provided in the invention.

BACKGROUND OF THE INVENTION

Electrophoresis is the movement of electrically charged particles in a fluid under the influence of an electric field. The particles migrate toward the electrode of the opposite electric charge. Electrophoresis separation is dependent on charge and molecular size of macromolecules.

DNA damage and repair is a normal phenomenon in a cell. Its assessment at a single cell level may provide an important diagnostic tool for evaluating the effect of exposure/susceptibility to chemicals/disease conditions as measured in the Comet assay (Alok Dhawan et. al. 2001. Mutation. Research, Fundamental and Molecular Mechanisms of Mutagenesis 474 (1-2) 121-128).

As of now the methods involved in electrophoresis are vertical and 2D gel mainly for proteins; horizontal gel electrophoresis—mainly for RNA and DNA; and rod electrophoresis for studying enzyme leakage. Bangalore Genei (http://www.bangaloregenei.com/pdf-08/Techware-08/G19.pdf) uses a circular anode for their Rod Gel apparatus, wherein the provision of running the proteins has been made in separate tubes/rods. However all these have a common principle that the nucleotide/protein is pulled in one direction under the electric field to resolve different bands/damage to these macromolecules. However the draw backs in these kinds of electrophoresis are as follows:
1. The electrical field is applied to a large surface area and hence it is not uniform
2. Due to the large size of the gel and device, it is not possible to conduct the experiments on the field as the device is not portable.
3. The current requirement for running the existing devices is very high thereby limiting their use only to the laboratory.
4. The resolution is unidirectional and therefore resolution of bands having close molecular weight is not feasible.
5. The existing devices use a large amount of platinum wire as well as other materials due to their size and hence are relatively expensive.

Conventionally, in electrophoresis including in Comet assay the electrical field is applied to a large surface area while the viewing area is very small, which, as far as uniformity of the field is concerned may not be appropriate.

To overcome these drawbacks a cost-effective apparatus is devised which is capable of resolving macro molecules in a circular multidirectional manner thus increasing resolving capacity of macromolecules in an efficient way. This is portable and uses a circular electrode facilitating maximum charge transfer.

This invention will have a major use for in vitro and in vivo genetic toxicology by assessing DNA damage in various living cells including lymphocytes, fibroblasts, macrophages, bladder cells, cervical epithelium and other eukaryotic cells as well as bacteria. Also the device shall be useful for the separation of different proteins, DNA and RNA of varying molecular weights. Due to small size of the device and simplicity of method thereof, it can be used at the field level for conducting human biomonitoring studies as well as for diagnostics.

This device and method will help in resolving nucleotides as well as proteins using circular electrophoresis. The circular electrode concept shall have better degree of resolution of bands of DNA, RNA and proteins in circular mode (360°), compared to the existing available technologies such as Comet assay where the DNA damage is measured only in one direction. Even DNA, RNA and protein gel electrophoresis is conducted in a single direction. This device and method will provide an opportunity to conduct electrophoresis in a circular mode (360°).

OBJECTS OF THE INVENTION

The main object of the present invention is a circular electrophoretic device for separation of charged molecules.

Another object of the present invention is to provide a method of resolving macromolecules in a circular multidirectional manner.

Still another object of the present invention is to provide a method of viewing macromolecules at a higher resolution.

Yet another object of the present invention is to provide a circular electrophoretic device for high resolution of biomolecules like DNA, RNA and proteins.

Still another object of the present invention is to provide a portable device to conduct electrophoresis in the field.

Yet another object of the present invention is to provide a device facilitating multiple sample analysis.

Still another object of the present invention is to provide a method for assessing DNA damage.

BRIEF DESCRIPTION OF FIGURES

The present invention is illustrated in FIG. 1 of the drawing(s) accompanying this specification. In the drawings like reference numbers/letters indicate corresponding parts in the various figures:

FIG. 2: Represents the outcome of the experiment conducted to assess DNA damage in human lymphocytes by invented device.

2A: This figure represents control human lymphocyte i.e. a normal cell without DNA damage.

2B: This figure represents treated human lymphocyte i.e. a cell with DNA damage as evident by the formation of concentric rings formed after running circular electrophoresis using the invented device. This is in contrast to the control cell which does not show such formation of rings. DNA damage assessed by the invented device in control (A) and treated (B) human lymphocytes showing rings of different molecular weight DNA fragments (B) at magnification 400×.

FIG. 3: Represents DNA gel electrophoresis in 1% agarose, the outcome of the experiment conducted on resolving different DNA fragments of varying molecular weights.

3A: Depicts the resolution of nine different fragments when 2 µg of DNA was loaded into the well and run at 10 mA/10V (constant current) for 1 hour in the circular electrophoretic chamber. Distance travelled by DNA was 2 cm.

3B: Depicts that when the same sample of DNA was run for 2 cm in the conventional way [Lanes 1, 2, 3, 4 containing 2, 1, 0.5, 0.3 µg of DNA respectively were run for 2 cm at 120V/55 mA (constant voltage)] in the horizontal gel apparatus only six bands were resolved.

3C: Depicts that to achieve similar resolution to that observed in circular electrophoresis (FIG. 3A), the gel had to be run for 8 cm at 120V/55 mA (constant voltage) in the horizontal gel apparatus (lanes 1, 2, 3, 4 containing 2, 1, 0.5, 0.3 µg of DNA respectively).

Figure 1:
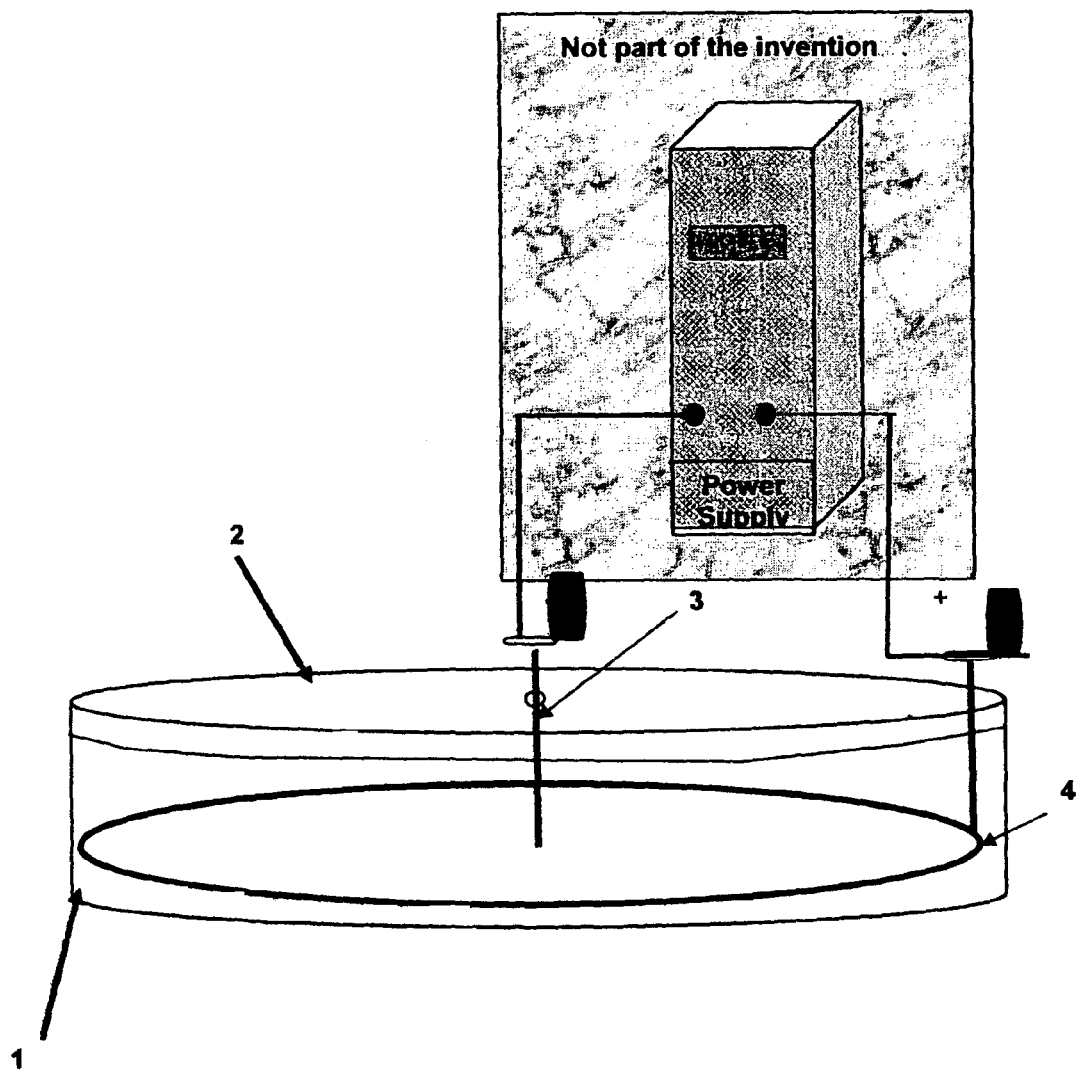
FIG. 1: Represents the drawing of the invention. The individual components are described below:
1. Petri dish of corrosion resistant material such as plastic/glass, etc.—is used as a electrophoresis tank
2. Lid—provides support to the central cathode as well as serves as a cover to prevent any shock.
3. Cathode—used as −ve electrode for transmission of electric current
4. Circular Anode—used as +ve electrode for transmission of electric current
Figure 4:
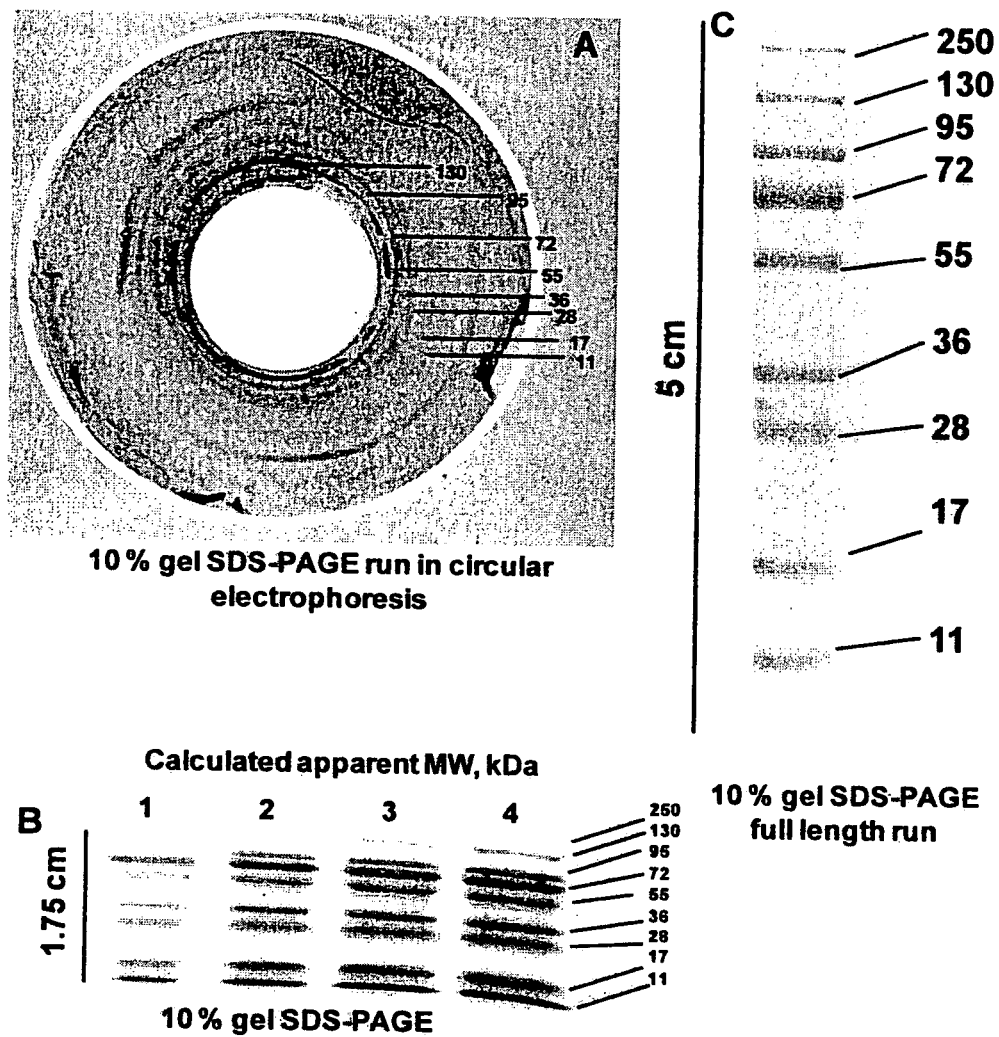

FIG. 4: Represents protein gel electrophoresis in 10% SDS-PAGE, showing bands of different sizes (kDa), the outcome of the experiment conducted on resolving different proteins of varying molecular weights.

4A: Represents gel electrophoresis in 10% SDS-PAGE, showing bands of different sizes (kDa) (20 µl of prestained protein ladder into the well and run at 13 mA/26V (constant current) for 4 hour) in the circular electrophoretic chamber. Distance travelled by protein was 1.75 cm and 8 proteins were resolved;

4B: Depicts that when the sample was run in vertical gel electrophoresis apparatus [lanes 1, 2, 3, 4 containing 5, 10, 15, 20 µl of prestained protein ladder respectively were run for 13 mA/26V (constant current) for 3 hour] the resolution was similar to that observed in the circular electrophoresis showing that the circular version is better;

4C: Depicts that when gel containing 20 µl of pre stained protein ladder was run for 5 cm at 35 mA/70V (constant current) in the vertical gel electrophoresis the bands were resolved better although we required more current and voltage to achieve this resolution in as compared to the circular version.

SUMMARY OF THE PRESENT INVENTION

Accordingly, the present invention provides a circular electrophoretic device useful for separation of charged molecules comprising of a chamber, lid, positive electrode and negative electrode and a process of electrophoresis hereof.

In an embodiment of the present invention, a circular electrophoretic device useful for separation of charged molecules comprising of a chamber, lid, positive and negative electrode.

In another embodiment of the present invention, the chamber is a circular petridish having the diameter in the range of 2-6 cm.

Yet in another embodiment of the present invention, one electrode is circular and present at the periphery of petridish.

Still in another embodiment of the present invention, the second linear electrode is supported in the centre of the lid of the petridish.

Yet in another embodiment of the present invention, the electrodes are made of oxidation resistant material preferably platinum.

Still in another embodiment of the present invention, the material used for making the petridish is made of corrosion resistant material selected from the group consisting of plastic, silica coming glass, inert materials etc.

Yet in another embodiment of the present invention, the device is useful for testing multiple samples.

Still in another embodiment of the present invention, the sample is selected from the group consisting of DNA, RNA and protein.

Yet in another embodiment of the present invention, the device is useful for separation of chemicals based on charge and molecular weight.

Still in another embodiment of the present invention, the device is useful to study mobilities based on circular charge of small organisms selected from the group consisting of microbes, protozoa.

Yet in another embodiment of the present invention, a kit for circular electophoresis, comprising a circular petridish chamber, said chamber having a circular and linear electrode, suitable buffers and instruction manual.

Still in another embodiment of the present invention, a process of electrophoresis using the circular electrophoretic device wherein the said process comprising of:
 a. casting a resolving gel of agarose on a slide,
 b. loading a sample in the center of the slide as prepared in step (a),
 c. placing the slide in center of chamber as claimed in claim 2.
 d. placing the electrodes attached to the lid as claimed in claim 3 and 4,
 e. applying current between the electrodes
Optionally,
 f. casting a polyacrylamide resolving gel and place it in the chamber as claimed in claim 2,
 g. loading sample in the center of the gel casted in step (a),
 h. placing the electrodes as claimed in claim 12(d) and (e).

Yet in another embodiment of the present invention, a power supply is in the range of 2-30V and current is in the range of 10-50 mA.

Still in another embodiment of the present invention, the electrophoresis is carried out multidirectionally)(360°).

Yet in another embodiment of the present invention, the process is useful for detecting molecules selected from the group consisting of DNA, RNA and protein.

DETAILED DESCRIPTION OF THE INVENTION

In present invention the device consists of a chamber and two electrodes between which current is passed. In the present invention the measurement of high resolution of macromolecules is depicted by measuring DNA damage. The chamber used for electrophoresis is a petridish having diameter of 2-6 cm. The Petri dish has a circular electrode at its periphery serving as an anode. The lid has been provided to support the other electrode cathode in the middle to create uniform circular electric field. The diameter of electrode ranges between 100 µm to 5 mm. The electrodes are made from corrosion resistant platinum. The power supply used in this portable device is 2V and 10 mA which is incidentally a dry cell. To provide constant current a positive temperature coefficient (PTC) has been incorporated in our circuit.

In the existing electrophoresis system, the electrical field is being applied to a large surface area while target viewing area is very small. The uniformity of the electrical field may not be appropriate to provide higher resolution. While DNA or cell for that matter is at the most 100 µm, the surface to which the electrical current is applied in the existing electrophoresis tanks is in the range of 20-30 cm. Hence in the present invention a petridish has been used as an electrophoresis apparatus instead of a tank. Our results of cell DNA experiments involving this device validate our claim of higher resolution.

Most of the devices of electrophoresis apparatus are uni- or bi-directional, which, may have inherent limitations. In case of comet assay a method to assess DNA damage in a cell the electrical field is applied in a single direction. However, it is well known that the DNA damage occurs all over. Hence the sensitivity is compromised. In the present invention, however, electrical field is applied using a circular electrode enabling assessment of DNA damage in all directions in the form of rings which are more sensitive. This claim is also proved from our experiments (FIG. 2).

One platinum electrode is fixed in the middle of the petridish and at the periphery of the dish a circular ring of platinum is placed. In our experiment, an electrical field of 2 volts was applied due to which the average lines of forces generated are circular and not linear as in the case of conventional electrophoresis system. Since the size of dish is small, a more uniform electrical field is generated compared to a conventional electrophoresis tank. Since the macromolecules are negatively charged we have placed the cathode in the middle and a circular anode at the periphery.

DNA damage and repair is a normal phenomenon in a cell. Its assessment at a single cell level may provide an important diagnostic tool for evaluating the effect of exposure/susceptibility to chemicals/disease conditions. DNA per se is tightly bound bundle of nucleotide chain. However in the event of strand breaks the bundle tends to loosen. Under the electrical field these breaks can be stretched out of the nucleus in the form of small DNA fragments enabling them to be quantified. However, conventionally the electrophoresis is done uni-directionally thereby limiting the resolution of assay. In the present invention this limitation has been circumvented by using a circular anode enabling to stretch out the fragments of macromolecules in all the directions)(360°. Each petridish would contain one sample and simultaneously 8-12 such petridishes (samples) when connected in series to a power supply would allow simultaneous detection of DNA damage from control as well as treated cells.

The following examples are given by way of illustration of the working of the invention in actual practice and therefore should not be construed to limit the scope of the present invention in any way.

Example-1

Making the Device

For making the device, a petridish of 5 cm diameter made of a material resistant to corrosion—silica corning glass is used. The petridish has a circular electrode made of platinum at its periphery. The diameter of electrode made of platinum wire is between 100 µm to 5 mm. The other electrode i.e. cathode, is made of platinum and supported in the center of the lid of the device. The lid is also made of silica glass material/plastic. This Petri dish is attached in series to the power supply.

Power supply: A regular power supply for adjusting 2-30V and 10-50 mA current is used.

Example-2

Gel Preparation for Comet Assay

Base slide is prepared by dipping the fully frosted slides (25 mm×25 mm) in hot (60° C.) 1.0% Normal Melting Agarose (dissolved in Milli Q water). The underside of the slide was wiped to remove the agarose and the slide placed on a flat surface to dry. (The slides are stored at room temperature until needed; avoiding humid conditions.)

Example-3

Sample Preparation and Loading on Gel for Comet Assay

The cells (CHO, human lymphocytes etc.) are treated in vitro and then washed before running the electrophoresis. Blood from control and exposed human/animal is collected in a heparinised tube and processed for isolation of lymphocytes. Other tissues are also processed for isolating and making a single cell suspension.

A single cell suspension of the cells of interest was obtained per se (in vivo) or after treatment (in vitro) in the medium suitable for the cells or phosphate buffered saline (PBS). 25 µl suspension is diluted 1:1 with 25 µl of 1% low melting agarose. 50 µl each is loaded onto each base slide (25 mm×25 mm) and a cover slip (22 mm×22 mm) placed on it. The slide was kept on ice packs for 5 minutes to allow the gel to solidify. Then, the cover-slip was removed and 5 µl of 0.5% low melting agarose (LMPA) at 37° C. was added onto the slide and again covered with a cover-slip. The slide was again put on ice packs to allow the gel to solidify.

Example-4

Electrophoresis for Comet Assay

The cover slips were removed and the slides put into the petridish filled with chilled lysing solution 5 ml. The lysing was done for at least two hours and then the lysing solution was removed completely. Freshly prepared chilled electrophoresis buffer (pH>13; 5 ml) was filled in the petridishes. Unwinding of DNA was done for a minimum of 20 minutes and then electrophoresis was carried out for 30 minutes at 4V and 10 mA current. Slides were then neutralized with chilled neutralization solution thrice each for 5 minutes. The slides were then dipped in chilled distilled water to remove excess alkali and stained with ethidium bromide for 5 minutes. The slides were again dipped in chilled distilled water to remove excess stain, and a fresh cover-slip (22 mm×22 mm) was put on them. The slides were read within 24 hours on a fluorescent microscope.

All the above steps were performed under dim yellow light to prevent DNA damage.

To Run the Experiment the Following Materials are Required:

Ethylene diamine tetraacetic acid disodium salt (EDTA), Ethidium bromide, Phosphate Buffered Saline (PBS; $Ca^{++}$, $Mg^{++}$ free), Sodium chloride (NaCl), Sodium hydroxide (NaOH), Triton X-100, Tris Buffer, Normal Melting Agarose (NMA), Low Melting Point Agarose (LMPA), Coplin jars (opaque), Microcentrifuge Tubes, Micropipettor and Tips, petridishes, Fully frosted slides (25 mm×25 mm) Coverslips (No. 1, 22×22 mm), Frozen ice packs, and Power pack.

The Working Solutions Used are as Follows:
1. Phosphate Buffered Saline (PBS; $Ca^{+2}$, $Mg^{+2}$ free).
2. Lysing Solution (stock; pH 10.0) consisting of NaCl, EDTA and Tris buffer. The final lysing solution is prepared fresh by adding 1% Triton X-100 to stock lysing solution.
3. Electrophoresis Buffer consisting of NaOH and EDTA.
4. Tris (pH 7.5) is used as Neutralization Buffer.
   Staining Solution Ethidium Bromide (EtBr)

Example-5

The device can resolve DNA fragments in a more efficient manner compared to the conventional horizontal gel electrophoresis (FIG. 3 A-C). As evident from the figure the circular gel electrophoresis device was able to resolve the DNA fragments of different molecular weights at a much lower voltage as well as current when compared to the same in the conventional method for the same distance (FIGS. 3 A & B). Moreover the resolution achieved at 2 cm in circular electrophoresis was comparable to that achieved by running the conventional gel for 8 cm (FIGS. 3A & C).

Example-6

The device is also capable of resolving proteins in a more efficient manner compared to the conventional vertical gel electrophoresis (FIG. 4 A-C). As evident from the figure the circular gel electrophoresis device was able to resolve the proteins of different molecular weights at a much lower voltage as well as current when compared to the same in the conventional method for the same distance (FIGS. 4 A & B). Moreover the resolution achieved at 2 cm in circular electrophoresis was comparable to that achieved by running the conventional gel for 5 cm (FIGS. 4 A & C).

ADVANTAGES

The main advantages of the present invention are:
1. It provides a device for higher resolutions of macromolecules.
2. It provides a uniform electrical field to act on the macromolecule.
3. It provides a portable device to conduct electrophoresis in the field.
4. It provides a device which is cost effective.
5. It provides a device to resolve DNA and proteins by applying a low current and voltage within a short distance.
6. The device enables flow of current in all directions to resolve macromolecules in circular multidirection manner.
7. The device allows different samples to be runned simultaneously in series.
8. The device is useful for in vitro and in vivo genetic toxicology assays by assessing DNA damage in various living cells.

We claim:

1. A circular gel electrophoretic device for resolving charged molecules comprising:
   a. a positive circular uniplanar electrode,
   b. a negative linear electrode, and
   c. a petri dish having a periphery, a center and lid to hold the electrodes in place, alone with gel and buffer;
wherein the positive circular uniplanar electrode is at the periphery of the dish and the negative linear electrode is in the center of the chamber supported by the lid, so that a circular electric field may be generated.

2. The device as claimed in claim 1, wherein said dish having a diameter in the range of 2-6 cm.

3. The device as claimed in claim 1, wherein the electrodes are made of inert materials preferably platinum.

4. The device as claimed in claim 1, wherein the material used for making the dish is made of inert corrosion resistant material selected from the group consisting of plastic, and silica corning glass.

5. The device as claimed in claim 1, wherein the device is useful for testing multiple samples.

6. The circular electrophoretic device as claimed in claim 5, wherein the device is useful for resolving DNA, RNA and proteins based on charge and molecular weight.

7. The device as claimed in claim 1, wherein the device is useful to study mobilities of microbes and protozoa based on circular charge.

8. A process of electrophoresis using the circular gel electrophoretic device as claimed in claim 1, comprising the steps of:
   a. placing the positive uniplanar circular electrode in the periphery of the dish,
   b. casting a gel in the dish,
   c. loading a sample in the center of the gel as prepared in step (b),
   d. placing the negative linear electrode attached to the lid, and
   e. applying current between the electrodes in the range of 10-50 mA and 2-30 Volts.

9. The process as claimed in claim 8, wherein the gel is prepared from the material selected from the group consisting of agarose, polyacrylamide and polymers.

10. The process as claimed in claim 8, wherein the electrophoresis is carried out uniplanar and multi-directionally (360°).

11. The process as claimed in claim 8, wherein the process is useful for detecting molecules selected from the group consisting of DNA, RNA and proteins.

12. A kit for circular gel electrophoresis, comprising:
   a petri dish having a periphery and a center,
      said dish having a positive uniplanar circular electrode and a negative linear electrode,
   suitable buffer and
   and instruction manual,
wherein the positive uniplanar circular electrode is at the periphery of the dish and the negative linear electrode is at the center of the dish, so that a circular electric field may be generated.

* * * * *